(12) United States Patent
Matthiessen et al.

(10) Patent No.: US 8,343,748 B2
(45) Date of Patent: Jan. 1, 2013

(54) PREPARATIVE PURIFICATION PROCESS FOR HUMAN FURIN

(75) Inventors: Peter Matthiessen, Vienna (AT); Stefan Romeder-Finger, Vienna (AT); Peter Turecek, Klosterneuburg (AT); Hans-Peter Schwarz, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1008 days.

(21) Appl. No.: 12/124,390

(22) Filed: May 21, 2008

(65) Prior Publication Data
US 2009/0304669 A1 Dec. 10, 2009

Related U.S. Application Data

(60) Provisional application No. 60/931,301, filed on May 22, 2007.

(51) Int. Cl.
*C12N 9/14* (2006.01)
*C07K 1/18* (2006.01)
*C07K 1/20* (2006.01)

(52) U.S. Cl. ...................... 435/212; 530/416
(58) Field of Classification Search .................. None
See application file for complete search history.

(56) References Cited

U.S. PATENT DOCUMENTS

| | | | |
|---|---|---|---|
| 5,460,950 A | 10/1995 | Barr et al. | |
| 5,935,815 A | 8/1999 | van de Ven et al. | |
| 5,989,856 A | 11/1999 | van de Ven et al. | |
| 6,210,929 B1 * | 4/2001 | Schlokat et al. | 435/69.7 |
| 6,274,365 B1 | 8/2001 | van de Ven et al. | |

FOREIGN PATENT DOCUMENTS

| | | |
|---|---|---|
| WO | WO 91/06314 A2 | 5/1991 |
| WO | WO 91/06314 A3 | 5/1991 |
| WO | WO 01/10896 A2 | 2/2001 |
| WO | WO 01/10896 A3 | 2/2001 |

OTHER PUBLICATIONS

Gordon V. et al. "Proteolytic activation of bacterial toxins by eukaryotic cells is performed by furin and by additional cellular proteases." Infect Immun. Jan. 1995;63(1):82-7.*
Chiron MF et al. Cleavage of Pseudomonas Exotoxin and Diphtheria Toxin by aFurin-like Enzyme Prepared from Beef Liver J. Biological Chem. 269(27):18167-18167, 1994.*
Bravo DA et al. "Accurate and Efficient Cleavage of the Human Insulin Proreceptor by the Human Proprotein-processing Protease Furin" J. Biological Chem. 269(41):25830-25837, 1994.*
Jang Hj et al "A novel subtilisin-like serine protease from Thermoanaerobacter yonseiensis KB-1: its cloning, expression, and biochemical properties" Extremophiles 6:233-243, 2002.*
Anderson et al. "Activation of the furin endoprotease is a multiple-step process: requirements for acidification and internal propeptide cleavage" The EMBO Journal vol. 16 No. 7 pp. 1508-1518, 1997.*

Bravo, D.A. et al., "Accurate and Efficient Cleavage of the Human Insulin Proreceptor by the Human Proprotein-processing Protease Furin," *The Journal of Biological Chemistry*, Oct. 14, 1994, vol. 269, No. 41, pp. 25830-25837.
GE Healthcare, "Capto MMC, Data file 11-0035-45 AA," 2005, located at <http://www.gelifesciences.co.jp/catalog_pdf_attach/11003545AA.pdf>, last visited on Feb. 17, 2009, 6 pages.
International Search Report mailed on Jan. 1, 2009, for International Application No. PCT/EP2008/004090 filed on May 21, 2008, 8 pages.
Merck, "Product Information 1.16887/1.16881 Fractogel® EMD TMAE (S), (M),", Jul. 25, 2003, located at <http://www.merck-chemicals.com/is-bin/INTERSHOP.enfinity/WFS/Merck-International-Site/en_US/-/USD/ViewProductDetail-Attachments?CatalogCategoryiD=&ProductUUID=SVeb.S10j2MAAAEWLIW4z8A&PortalCatalogUUID=Uc6b.s1LfzAAAEW6tYfVhTI&SelectedDocumentType=TI#ankerTechnicalInfo>, last visited on Feb. 17, 2009, 1 page.
Preininger, A. et al., "Strategies for recombinant Furin employment in a biotechnological process: complete target protein precursor cleavage," *Cytotechnology*, 1999, vol. 30, pp. 1-15.
Anderson, E.D. et al., "Activation of the Furin Endoprotease is a Multiple-Step Process: Requirements for Acidification and Internal Propeptide Cleavage," *The EMBO Journal*, 1997, vol. 16, No. 7, pp. 1508-1518.
Bresnahan, P.A. et al., "Huam *fur* Gene Encodes a Yeast KEX2-like Endoprotease That Cleaves Pro-β-NGF In Vivo," *The Journal of Cell Biology*, Dec. 1, 1990, vol. 111, No. 6, pt. 2, pp. 2851-2859.
Cameron, A. et al., "Polyarginines Are Potent Furin Inhibitors," *The Journal of Biological Chemistry*, Nov. 24, 2000, vol. 275, No. 47, pp. 36741-36749.
Creemers, J.W.M. et al., "Modulation of Furin-Mediated Proprotein Processing Activity by Site-Directed Mutagenesis," *The Journal of Biological Chemistry*, Oct. 15, 1993, vol. 268, No. 29, pp. 21826-21834.
Hatsuzawa, K. et al., "Molecular and Enzymatic Properties of Furin, a Kex2-Like Endoprotease Involved in Precursor Cleavage at Arg-X-Lys/Arg-Arg Sites," *J Biochem*, 1992, vol. 111, No. 3, pp. 296-301.
Hatsuzawa, K. et al., "Purification and Characterization of Furin, a Kex2-like Processing Endoprotease, Produced in Chinese Hamster Ovary Cells," *The Journal of Biological Chemistry*, Aug. 15, 1992, vol. 267, No. 23, pp. 16094-16099.

(Continued)

*Primary Examiner* — Mary E Mosher
*Assistant Examiner* — Nianxiang (Nick) Zou
(74) *Attorney, Agent, or Firm* — Marshall, Gerstein & Borun LLP (57) ABSTRACT

Recombinant truncated human furin was expressed in CHO cells and concentrated approximately 50-fold by ultrafiltration and diafiltration. The concentrate was purified by column chromatography on CAPTO MMC™ (mixed cation exchange/hydrophobic interaction gel) resulting in a 30-50 fold purification factor and a yield of at least 60%. The at least 20% pure preparation obtained after CAPTO MMC™ (mixed cation exchange/hydrophobic interaction gel) chromatography had already a purification degree allowing on-column maturation of pro-VWF. Then an additional Arginine Sepharose chromatography purification was carried out. This two column process for purification of truncated human furin resulted in an almost pure furin preparation with a specific activity of approximately 290,000 U furin/mg protein and a yield of about 50%.

13 Claims, 4 Drawing Sheets

OTHER PUBLICATIONS

Hosaka, M. et al., "Arg-X-Lys/Arg-Arg Motif as a Signal for Precursor Cleavage Catalyzed by Furin Within the Constitutive Secretory Pathway," *The Journal of Biological Chemistry*, Jul. 5, 1991, vol. 266, No. 19, pp. 12127-12730.

Leduc, R. et al., "Activation of Human Furin Precursor Processing Endoprotease Occurs by an Intramolecular Autoproteolytic Cleavage," *The Journal of Biological Chemistry*, Jul. 15, 1992, vol. 267, No. 20, pp. 14304-14308.

Molloy, S.S. et al., "Human Furin is a Calcium-Dependent Serine Endoprotease That Recognizes the Sequence Arg-X-X-Arg and Efficiently Cleaves Anthrax Toxin Protective Antigen," *The Journal of Biological Chemistry*, Aug. 15, 1992, vol. 267, No. 23, pp. 16396-16402.

Nakayama, K., "Purification of Recombinant Soluble Forms of Furin Produced in Chinese Hamster Ovary Cells," Chapter 12 in *Methods in Enzymology*, 1994, vol. 244, pp. 167-175.

Nakayama, K., "Furin: A Mammalian Subtilisin/Kex2p-like Endoprotease Involved in Processing of a Wide Variety of Precursor Proteins," *Biochem J.*, 1997, vol. 327, pp. 625-635.

Plaimauer, B. et al., "Shed' Furin: Mapping of the Cleavage Determinants and Identification of Its C-Terminus," *Biochem J*, 2001, vol. 354, pp. 689-695.

Rehemtulla, A. et al., "Preferred Sequence Requirements for Cleavage of Pro-von Willebrand Factor by Propeptide-Processing Enzymes," *Blood*, May 1, 1992, vol. 79, No. 9, pp. 2349-2355.

Teuchert, M. et al., "Sorting of Furin at the Trans-Golgi Network," *The Journal of Biological Chemistry*, Mar. 19, 1999, vol. 274, No. 12, pp. 8199-8207.

Van De Ven, W.J.M. et al., "Furin is a Substillisin-like Proprotein Processing Enzyme in Higher Eukaryotes," *Molecular Biology Reports*, 1990, vol. 14, pp. 265-275.

Verweij, C.L. et al., "Full-Length von Willebrand Factor (vWF) cDNA Encodes a Highly Repetitive Protein Considerably Larger Than the Mature vWF Subunit," *The EMBO Journal*, 1986, vol. 5, No. 8, pp. 1839-1847.

Vey, M. et al., "Maturation of the *trans*-Golgi Network Protease Furin: Compartmentalization of Propeptide Removal, Substrate Cleavage, and COOH-terminal Truncation," *The Journal of Cell Biology*, Dec. 1, 1994, vol. 127, No. 6, Pt. 2, pp. 1829-1842.

Vidricaire, G. et al., "Characterization of a Secreted Form of Human Furin Endoprotease," *Biochemical and Biophysical Research Communications*, Sep. 15, 1993, vol. 195, No. 2, pp. 1011-1018.

Wasley, L.C. et al., "PACE/Furin Can Process the Vitamin K-dependent Pro-factor IX Precursor Within the Secretory Pathway," *The Journal of Biological Chemistry*, Apr. 25, 1993, vol. 268, No. 12, pp. 8458-8465.

Wise, R.J. et al., "Expression of a Human Proprotein Processing Enzyme: Correct Cleavage of the von Willebrand Factor Precursor at a Paired Basic Amino Acid Site," *Proc. Natl. Acad. Sci. USA*, Dec. 1990, vol. 87, 9378-9382.

\* cited by examiner

PREPARATIVE PURIFICATION PROCESS FOR HUMAN FURIN

FIELD OF THE INVENTION

The present invention relates to purification methods of a recombinant human furin, a truncated human furin or a furin derivative which is used for the processing of inactive precursor proteins to mature proteins.

BACKGROUND OF THE INVENTION

The family of the proteolytic mammalian subtilisin-like proprotein convertases (SPC or PC) is homologous with bacterial subtilisins and yeast Kex2p. To date seven distinct members of the SPC family have been identified, including furin, PC1 (also known as PC3), PC2, PACE4, PC4, PC5 (also known as PC6), PC7 (LPC, PC8, or SPC7), each of which exhibits unique tissue distribution.

All SPCs are multidomain enzymes, composed of an amino-terminal propeptide, a subtilisin-like catalytic domain, a middle domain and a unique carboxy-terminus composed of one or more domains. The pro-, catalytic and middle domains are essential and sufficient for catalytic activity. The carboxy-terminal domains are thought to contain the information for correct targeting to, and concentration in, the compartment of the secretory pathway in which the enzymes function.

These proteins have been implicated in the endoproteolytic maturation processing of inactive precursor proteins including hormones, growth factors, receptors, viral and bacterial proteins, and plasma proteins such as albumin, von Willebrand Factor (VWF), factor VII, factor IX, and factor X at single, paired or multiple basic consensus sites (Nakayama, Biochem J., 1997; 327:625-35).

The SPC member furin, also termed PACE (paired basic amino acid cleavage enzyme) is ubiquitously expressed in all mammalian tissues and cell lines and is capable of processing a wide range of bioactive precursor proteins in the secretory pathway, including also hormones, growth factors, receptors, viral and bacterial proteins, and plasma proteins. It is a calcium-dependent serine endoprotease structurally arranged into several domains, namely a signal peptide, propeptide, catalytic domain, middle domain, (also termed homo-B or P-domain), the C-terminally located cysteine-rich domain, transmembrane domain and the cytoplasmic tail. The furin protease cleavage site comprises a recognition sequence which is characterized by the amino acid sequence Arg-X-Lys/Arg-Arg (Hosaka et al., J Biol Chem. 1991; 266:12127-30).

Intact furin is incorporated into the membrane system of the Golgi apparatus and there it is functionally active (Bresnahan et al., J Cell Biol. 1990; 111:2851-9). Upon transit of the newly synthesized furin precursor from the endoplasmic reticulum to the Golgi compartment, the propeptide is autocatalytically removed in a two step processing event (Anderson et al., EMBO J. 1997; 16:1508-18).

Furin also cycles between the trans-Golgi network and the cell surface via endosomal vesicles, thereby processing both precursor proteins during their transport through the constitutive secretory pathway as well as molecules entering the endocytic pathway. The cellular distribution of furin to the processing compartments is directed by defined structural features within its cytoplasmic tail (Teuchert et al., J Biol Chem. 1999; 274:8199-07).

Since an overexpression of the protease negatively affects the growth of continuously growing cell cultures, solutions have been sought to reduce the toxic influence of furin on the cells. The C-terminal domains have been found to be dispensable for the functional activity of furin and a truncated form of the over-expressed native furin of 75-80 kD could be detected in the cell supernatant as secreted protein (Wise et al., PNAS. 1990; 87:9378-82). This naturally secreted truncated furin is also known as "shed furin" (Vidricaire et al., Biochem Biophys Res Comm. 1993; 195:1011-8; Plaimauer et al., Biochem J. 2001; 354:689-95) and is cleaved N-terminally of the transmembrane portion (Vey et al., J Cell Biol. 1994; 127:1829-42).

Furin proteins truncated by genetic engineering, in which the encoding part of the transmembrane and cytoplasmatic domains has been deleted have been described for example for amino acids Δ714-794 (Leduc et al., J Biol Chem. 1992; 267:14304-8; Molloy et al., J Biol Chem. 1992; 267:16396-402) and for amino acids Δ716-794 ("Sol-PACE", Wasley et al., J Biol Chem. 1993; 268:8458-65; Rehemtulla and Kaufman, Blood. 1992; 79:2349-55) and for amino acids Δ705-794 (Hatsuzawa et al., J Biol. Chem. 1992; 267:16094-9). Furin mutants additionally comprising a deletion of the cystein-rich region have also been described (Hatsuzawa et al., J Biochem. 1992; 101:296-301; Creemers et al., J Biol Chem. 1993; 268:21826-34).

For biotechnological use in vitro as well as in vivo applications of SPCs are conceivable, including an application within the framework of a therapeutic treatment. For such applications, human furin or truncated furin may be more suitable than endopeptidases of non-human origin.

Furin or truncated furin may be applicable in the commercial production of all sorts of biologically active substances (e.g., other enzymes) if processing is a production step therein. For example the University of Leuven holds patents for the application of furin in the industrial production of biomedical relevant products (U.S. Pat. Nos. 5,989,856, 5,935,815, and 6,274,365).

Another example is the processing of pro-VWF. Actually the endoproteolytic activity of furin and its selectivity for basic amino acids has first been determined in experiments with pro-VWF. Pro-VWF consists of a propolypeptide with 741 amino acids and mature VWF with 2050 amino acids (Verweij et al., EMBO J. 1986; 5:1839-47) and is processed into its mature form by endogenously occurring furin (Wise et al., PNAS 1990; 87:9378-82; Van de Ven et al., Mol Biol Rep. 1990; 14:265-75; Rehemtulla and Kaufman, Blood. 1992; 79:2349-55). Because in the downstream process recombinant VWF (rVWF) consists of up to 50-70% of pro-rVWF, not fully maturated pro-rVWF has then to be further processed in vitro. Maturation of pro-rVWF can be achieved by addition of CHO cell supernatant containing unpurified furin to supernatant of unpurified pro-rVWF. However, due to low pro-rVWF and furin concentrations, this maturation process can last up to several days and is not very reproducible. Thus a purified furin or furin derivative would be preferable for the maturation process.

Despite the potential widespread use of furin or truncated furin in the maturation of proteins surprisingly there are only a few disclosures of methods for the purification of furin.

Recombinant truncated mouse furin has been purified only by a factor of 7 with a yield of 27% by purification with an anion exchange membrane followed by Mono Q and Superose 12 columns (Cameron et al., J Biol Chem. 2000; 275:36741-9).

Hatsuzawa et al. (J Biol Chem. 1992; 267:16094-9) achieved a 100-fold purification of truncated mouse furin in CHO cells with a relatively small yield of about 10% by using ammonium sulfate fractionation, TOYOPEARL® AF-Blue batchwise fractionation and DEAE-TOYOPEARL® chromatography. The same method was also used by Nakayama et al. as published in Methods Enzymol. 1994; 244:167-75.

All these methods, however, due to the use of several consecutive steps are either relatively time consuming, have a low purification degree or a low yield of furin. Such furin purification methods are not useful for a large scale industrial process where furin is only needed on top of the protein to be prepared. Thus there is a great need in the art for a fast furin purification process in combination with a high purification degree and a high yield. It was an inventive task of the present invention to develop a simple single column purification step for human recombinant furin or truncated furin with a high yield and sufficient purification degree to allow maturation of pro-proteins such as for example pro-rVWF. Furthermore, a subsequent additional purification step should be developed to obtain an essentially pure furin or truncated furin.

SUMMARY OF THE INVENTION

Furin, also termed PACE (paired basic amino acid cleavage enzyme) which is a member of the subtilisin-like proprotein convertases is ubiquitously expressed in all mammalian tissues and cell lines and is capable of processing a wide range of bioactive precursor proteins in the secretory pathway. Furin or truncated furin may be applicable in the commercial production of all sorts of biologically active substances if processing of pro-proteins is a production step therein. Despite the potential widespread use of furin or truncated furin in the maturation of proteins there are only a few purification methods for furin available, which are not optimal. To develop an improved purification method for furin recombinant truncated human furin was expressed in CHO cells and concentrated approximately 50-fold by ultrafiltration and diafiltration. The concentrate could be purified by column chromatography on CAPTO MMC™ resulting in a 30-50 fold purification factor and a yield of at least 60%. The at least 20% pure truncated furin preparation obtained after CAPTO MMC™ chromatography had already a purification degree allowing on-column maturation of pro-von Willebrand Factor. An additional Arginine Sepharose chromatography purification was also carried out. The two column process for purification of truncated human furin resulted in an almost pure preparation with a specific activity of approximately 290,000 U furin/mg protein and a yield of about 50%.

DETAILED DESCRIPTION OF THE INVENTION

The term "furin" is well defined in the art, examples can be found in the Swiss-Prot/TrEMBL data base (Accession NO P09958 and in one embodiment of the invention the furin means the peptide disclosed in and encoded by the DNA sequences disclosed in U.S. Pat. No. 5,986,079.

The term "furin derivative" includes truncated fragments of the furin amino acid (also termed "shed furin"), naturally occurring variants or deliberately modified sequences thereof. Thus also all proteins which have been generated from furin or the truncated furin analogue by insertion, deletion or exchange of amino acids and which have a furin-like biologic activity may be purified with the methods of the present invention.

In an embodiment of the invention the furin and furin derivative is produced by recombinant technology, i.e. by expressing DNA coding for such furin or furin derivative in an appropriate host cell transformed with such DNA.

A truncated furin of the present application may be generated by truncation of the DNA coding for furin at its 3'-terminus and/or its 5'-terminus while retaining the sequences coding for he furin endopeptidase activity. It may be desirable to delete the coding sequence for the transmembrane (TM) region and/or the cysteine-rich region (CRR). It also may be desirable to remove the region encoding the signal sequence, and/or to replace it with a heterologous sequence. A truncated furin according to the present invention may also contain a putative transmembrane domain which may serve to anchor it in the membranes of the Golgi apparatus.

It may also be desirable to ligate a portion of the furin DNA sequence (particularly a portion including the coding region for catalytic domain) to a heterologous coding sequence, and thus to create a fusion peptide with the enzymatic specificity of furin.

In a preferred embodiment of the present invention a truncated furin is of human origin and C-terminally truncated lacking amino acids 578 to 794 from the amino acid sequence of wild-type human furin as disclosed for example in U.S. Pat. No. 5,986,079. A truncated furin according to the present invention is truncated in a way that it can be expressed in high amounts in a cell without being substantially toxic to the cell. Such truncated furins are known in the art.

A furin, truncated furin, or furin derivative purified with the methods disclosed in the present invention may be used to prepare proteins from pro-proteins by proteolytical cleavage. Pro-proteins are intended to include all the precursors of proteins, which can be converted into functional proteins by suitable proteolytic treatment. In particular, pro-proteins may be pro-enzymes, pre-pro-enzymes or other (inactive) precursors of biochemically, physiologically or biotechnologically usable proteins or enzymes.

Examples of precursor polypeptides include, but are not limited to coagulation factors, such as VWF, factor IX, protein C, protein S, prothrombin, factor X, factor VII and bone gamma-carboxyglutamate protein, insulin, growth factors, such as platelet derived growth factor (PDGF) and nerve growth factor (NGF).

The production of a furin, truncated furin, or furin derivative according to the present application may include any method known in the art for the genetic engineering of recombinant DNA coding for such protein, e.g. via reverse transcription of RNA and/or amplification of DNA followed by a variety of methods for transfection of the vectors and recombinant expression of the protein. All the usual eukaryotic expression systems, such as a variety of vectors, permanent cell lines or viral expression systems may be used. The recombinant DNA coding for a furin, truncated furin, or furin derivative, e.g. a plasmid, may also contain a DNA sequence encoding a selectable marker for selecting the cells which have been successfully transfected with the plasmid.

Cell lines for the recombinant production of a furin, furin derivative or truncated furin according to the invention can be produced by stable integration of the exogenous DNA into the chromosome of the host cell. The host cell type may be any eukaryotic cell. In one embodiment the cell is a mammalian cell with the ability to perform posttranslational modifications of a furin, truncated furin, or furin derivative. For example said mammalian cell is derived from a mammalian cell line, like for example a cell line selected from the group consisting of SkHep-, CHO-, HEK293-, and BHK-cells. As the eukaryotic expression systems, also yeasts, and other cell types which express endogenous furin, truncated furin, or furin derivatives, may be used. Also transgenic animals can be used for the expression of a furin or of derivatives thereof. For the expression of recombinant proteins, CHO-DUXS B11 cells have proved particularly suitable (Urlaub et al., PNAS 1980; 77:4216-20). The cells may be cultured in any scale. In one specific example CHO cells were cultured by chemostat fermentation in 80-200 L scale.

There is no particular limitation to the media, reagents and conditions used for culturing the cells in the present invention. The cells may be cultured in a continuous or batch-wise manner with serum, but also under serum-free or serum- and protein-free conditions.

A furin according to the present invention can be isolated from cells by lysis and further purified by conventional methods, optionally in the presence of protease inhibitors. Furin is active in a relatively acidic medium with a pH of 5.5, as occurs in secretory granula, but the protein maintains its activity also at pH 7.5. The activity of furin depends on the presence of $Ca^{2+}$ ions. For the in vitro enzyme activity, a calcium concentration of 2-5 mM has been found to be optimal. The presence of metal chelators such as EDTA will greatly inhibit the activity of furin.

The evaluation of proteolytic activity of a furin, truncated furin or furin derivative can be performed by any suitable test, for example by using fluorogenic substrates which are comprised of a dibasic cleavage site for which furin is specific (Schlokat et al., Biotechnol Appl Biochem. 1996;24:257-67). With said assay 1 Unit is defined as the amount of furin that will release 1 pmol of 7-Amino-4-methylcoumarin (AMC) from the fluorogenic substrate Boc-Arg-Val-Arg-Arg-AMC (SEQ ID NO:2) in 1 minute at 30° C. Alternatively the proteolytic activity can also be measured by incubating furin with pro-proteins, for example pro-rvWF, for a sufficient time. The degree of pro-rvWF processing can be analyzed for example by Western blotting.

The present invention provides for a method for purifying recombinantly produced furin from the cell culture medium. A furin, truncated furin, or furin derivative can be surprisingly and advantageously purified by means of an anion exchange resin with a potential to bind furin at pH 6.0 such as the pressure-stable chromatography gels FRACTOGEL® EMD TMAE 650 (Merck, Darmstadt, Germany) and CAPTO Q™ (GE Healthcare, Freiburg, Germany).

In one embodiment of the invention it was found that CAPTO Q™ is surprisingly efficient for use in the capture and intermediate purification of high expression and high volume feeds of furin, truncated furin, or furin derivative. The highly rigid matrix allows a wider working range of flow velocities, bed heights and sample viscosities, all of which positively influence processing costs. High flow velocities increase volume throughput and reduce process time; longer bed heights eliminate the need for large equipment and keep footprints small; and high-flow processing of viscous samples means less dilution and shorter cycle times.

In another embodiment of the present application CAPTO MMC™ (GE Healthcare, Freiburg, Germany) resin was used. By using said resin surprisingly high purification factors of 30-50, high yields of at least 60%, and a specific activity of at least 100,000 U/mg of protein could be obtained with a single purification step.

In yet another embodiment of the present invention truncated furin purified on a CAPTO MMC™ resin was further purified on a Arginine Sepharose resin such as the ARGININE SEPHAROSE™ 4B column (GE Healthcare). By using said two resins surprisingly a high purification factor of 140, high yields of 50%, a purification factor of approximately 140, a purity of at least 90-95%, and a specific activity of 290,000 U/mg protein could be obtained.

A variety of buffer systems can be used for buffering furin, truncated furin, or furin derivatives and equilibrating the columns used in the present invention. In general every buffer having buffer capacity at pH 6.0 can be used. This includes e.g. phosphate, citrate, and Tris buffers. In one embodiment of the present invention the buffer is 50 mM Hepes/1 mM $CaCl_2$ and in another embodiment 10 mM sodium acetate/1 mM $CaCl_2$. The pH is in the range from 5.5 to 8.0 and in another embodiment the pH is 6.0.

The invention also includes a pharmaceutical composition comprising a endoproteolytically active amount of a furin, a truncated furin, or a furin derivative purified according to the present invention, and a pharmaceutically acceptable carrier. The carrier may be preferably a liquid formulation, and is preferably a buffered, isotonic, aqueous solution. A furin, truncated furin, or furin derivative purified according to the present invention can be provided as a pharmaceutical preparation having a furin polypeptide as a single component preparation or in combination with other components as a multiple component system, as for example the pro-proteins of VWF.

Pharmaceutically acceptable carriers also include excipients, such as diluents, and the like, and additives, such as stabilizing agents, preservatives, solubilizing agents, and the like. The polypeptides of this invention may be also in the form of any pharmaceutically acceptable salt.

As used herein, the term "pharmaceutically acceptable" means approved by a regulatory agency of US or EU government or listed in the U.S. Pharmacopeia or other generally recognized pharmacopeia for use in animals, and more particularly in humans.

The following examples illustrate the present invention but do not limit the scope of the invention in any way. Variations within the knowledge of one skilled in the art are to be considered to fall within the scope of the present invention.

EXAMPLES

Example 1

Expression and Analysis of Recombinant Truncated Furin

Truncated human furin lacking amino acids 578 to 794 (SEQ ID NO:1) was expressed in CHO cells which were cultured by chemostat fermentation in 80-200 L scale. A furin-containing CHO cell supernatant was concentrated approximately 50-fold (ultrafiltration unit with a 0.6 m² Hydrosart 30 kDa membrane, Sartorius Göttingen, Germany) and diafiltrated against 50 mM Hepes, 1 mM $CaCl_2$, pH 6.0 and stored at −20° C. and until use (within a week).

The protein content of the samples was measured according to the principle described by Bradford (Anal Biochem. 1976; 72:248-54) using the Protein Assay Dye Reagent Concentrate from Bio-Rad Laboratories (Hercules, Calif., USA).

The microassay procedure was carried out according to the manufacturer's instructions and calibrated using a certified human serum preparation (Qualitrol HS—N, DiaSys Diagnostics, Holzheim, Germany), obtaining a calibration range of 20 to 1.8 µg protein/mL. Concentrated samples were diluted in 0.9% NaCl.

The enzymatic furin activity of was determined in a fluorogenic assay. With this assay 1 Unit is defined as the amount of furin that will release 1 pmol of 7-Amino-4-methylcoumarin (AMC) from the fluorogenic substrate Boc-Arg-Val-Arg-Arg-AMC (SEQ ID NO:2) in 1 minute at 30° C. Recombinant furin standard (New England Biolabs, Ipswich, Mass., U.S.A.) was diluted 1:10, 1:20, 1:40, 1:80, 1:160, and 1:320 in 100 mM Hepes, 0.5% Triton X-100, 1 mM $CaCl_2$, 1 mM 2-Mercaptoethanol, pH 7.5). 150 µL of the diluted samples were shaken with 50 µL substrate (Boc-Arg-Val-Arg-Arg-AMC (SEQ ID NO:2) acetate salt; Bachem Distribution Service GmbH; Weil am Rhein, Germany) for 120 minutes at 30° C. in a black microliter plate for fluorescence applications. The release of AMC was measured in a fluorescence spectrophotometer at 360 nm/460 nm within 10 minutes after incubation. Furin concentrations were calculated using a reference curve with furin.

The contaminating CHO proteins were determined in a two-site sandwich ELISA assay format using an excess detection antibody and single incubation multilayer immune technique SIMIT (Naser, Immunol Methods. 1990; 129:151-7). Host cell antigen was prepared from cell culture supernatant of the non-recombinant progenitor CHO cell line DUKX. Polyclonal antibodies against the host cell antigens were raised in goats. For coating a 1:500 solution of goat anti-CHO antibody (in-house preparation) in coating buffer (100 mM sodium carbonate, 100 mM sodium hydrogen carbonate, adjusted to pH 9.5 with HCl) was used. PBST (137 mM NaCl, 2.7 mM KCl, 1.5 mM potassium dihydrogen phosphate, 7 mM disodium hydrogenphosphate dehydrate, 0.5 mL Tween 20, 0.1% bovine serum albumin, and 2 mM benzamidine) was used for sample dilution and blocking. A combination of an in-house biotinylated antibody (goat anti-CHO biotin) and streptavidin-peroxidase (Dako, Glostrup, Denmark) was used for detection using 3,3',5,5'-Tetramethylbenzidine (TMB) as substrate. The affinity purified host cell preparation was used as the assay standard (CHO-protein assay standard, 380 ng/mL, in-house preparation) covering an assay calibration range of 95 ng/mL to 3 ng/mL CHO protein. Samples were determined after logarithmic transformation of the ODs and the CHO protein concentrations of the standard dilutions and calculation of a linear regression curve.

The endotoxin content of a truncated furin preparation was determined in a Limulus Amebocyte Lysate (LAL) assay. The LAL contains an enzyme system which is activated in the presence of endotoxin. Briefly, the activated enzymes split off para-nitro aniline (pNA) from the chromogenic substrate S-2423 (Ac-Ile-Glu-Gly-Arg-pNA.HCl (SEQ ID NO:3), CoaChrom Diagnostica GmbH, Vienna, Austria) to produce a yellow colour. The pNA release is measured kinetically in an ELISA reader at 405 nm. Endotoxin concentration is calculated using a reference curve with endotoxin standard (*E. coli* 0111:B4).

Example 2

Identification of CAPTO MMC™ Resin as Single Column Purification Step

A truncated furin expressed and analyzed as described above was purified in comparison on different chromatography resins previously not used for furin or truncated furin preparation. Two anion exchange resins, i.e. FRACTOGEL® EMD TMAE 650 (Merck, Darmstadt, Germany) and CAPTO Q™ (GE Healthcare, Freiburg, Germany) and a mixed cation exchange/hydrophobic interaction gel (CAPTO MMC™) (GE Healthcare) were tested for purification and concentration potential of truncated furin derived from CHO cell supernatant. The chromatography runs were carried out with 50 mM Hepes/1 mM $CaCl_2$ buffer at a pH of 7.5 (FRACTOGEL® EMD TMAE 650 and CAPTO Q™) and 5.5-8.0 (CAPTO MMC™). A truncated furin column load and the conductivity was varied for the individual chromatography runs (Table 1). Bound furin was eluted using a linear 0-500 mM NaCl gradient in loading buffer within 15 CV. It should be noted that all truncated furin samples prepared were free of endotoxins.

TABLE 1

Comparison of Truncated Furin Purification with Different Chromatography Resins

| Column | Load (U/mL Gel) | Conductivity (mS/cm) | Recovery (%) | Spec. Activity (U/mg) | Purification (Factor) | CHO-Protein Removal (Factor) |
|---|---|---|---|---|---|---|
| TMAE | 2,705 | 6.7 | 36 | n.d. | n.d. | 1.3 |
| TMAE | 4,016 | 5.2 | 57 | 2,248 | 2.4 | 1.7 |
| TMAE | 4,403 | 4.8 | 46 | 2,533 | 3.0 | 1.7 |
| TMAE | 10,635 | 5.2 | 37 | 2,049 | 2.5 | 2.4 |
| TMAE | 32,625 | 5.0 | 68 | 10,011 | 5.3 | 2.4 |
| Capto Q | 16,847 | 4.5 | 45 | 8,797 | 7.4 | 5.5 |
| Capto Q | 33,781 | 4.8 | 51 | 14,138 | 8.9 | 5.0 |
| Capto Q | 21,860 | 4.5 | 71 | 7,789 | 7.1 | 4.5 |
| Capto MMC | 5,358 | 4.3 | 56 | 38,611 | 30.3 | 96 |
| Capto MMC | 13,218 | 3.9 | 63 | 110,424 | 37.6 | 56 |
| Capto MMC | 6,972 | 7.8 | 76 | 27,693 | 27.1 | 45 |

Because the results for the different columns were relatively homogenous within each group means were calculated for a better overview. The means of the 5 experiments with FRACTOGEL® EMD TMAE 650, 3 with CAPTO Q™, and 3 with CAPTO MMC™, respectively, are shown in Table 2.

TABLE 2

Overview of Comparison of Truncated Furin Purification
with Different Chromatography Resins

| Column | Recovery (%) | Spec. Activity (U/mg) | Purification (Factor) | CHO-Protein Removal (Factor) |
|---|---|---|---|---|
| TMAE | 49 | 4,210 | 3.3 | 1.9 |
| Capto Q | 56 | 10,241 | 7.8 | 5.0 |
| Capto MMC | 65 | 58,909 | 32 | 66 |

Whereas FRACTOGEL® EMD TMAE 650 and CAPTO Q™ could increase the purity of truncated furin by a factor of 3 and 8, respectively, CAPTO MMC™ resulted in a purification factor of 32. Truncated furin yield in the column eluate was 65% for CAPTO MMC™, 56% for CAPTO Q™ and 49% for FRACTOGEL® EMD TMAE 650.

Figure 4:
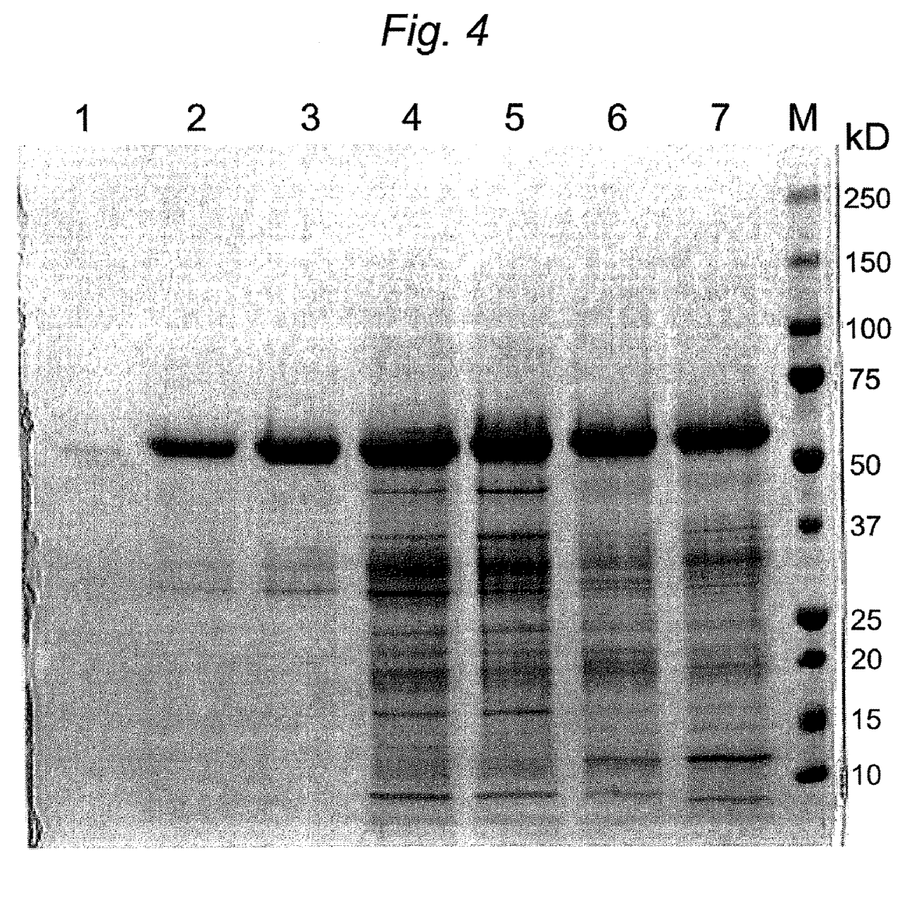
FIG. 4 shows the SDS-PAGE separation of a truncated furin purified by CAPTO MMC™ and CAPTO MMC™ in combination with Arginine Sepharose columns (Example 2 and Example 6)

In addition to the high purification factor of truncated furin the use of CAPTO MMC™ also resulted into the highest factor of removal of contaminating CHO proteins. As measured by COOMASSIE®-stained bands on a 8-18% gradient SDS-gel truncated furin was at least 20% pure. Typical examples are shown in FIG. 4: 3μg of different truncated furin preparations of CAPTO MMC™ eluates were loaded on lanes 4-7 (Lane 1: furin standard, lanes 2 and 3: Arginine Sepharose eluates, M=molecular weight marker.

Example 3

Replacement of Hepes Buffer by Sodium Acetate Buffer

To reduce buffer costs (approximately 500 per 1 L column) alternative buffer systems were tested. A reduction in Hepes concentration was not possible, because it resulted in substantial break-through of truncated furin in column flow-through and wash fraction. CAPTO MMC™ columns were loaded with 5,000-30,000 U furin/mL gel and eluted using a 0-500 mM NaCl gradient in loading buffer within 15 CV.

Several buffer systems were tested and it was found that 10 mM sodium acetate could achieve at least a similar purification factor, yield and capacity as compared to 50 mM Hepes buffer. The mean of three experiments using either Hepes or sodium acetate buffer is shown in Table 3.

TABLE 3

Comparison of Hepes and Sodium Acetate Buffer

| Buffer | Recovery (%) | Spec. Activity (U/mg) | Purification (Factor) | CHO-Protein Removal (Factor) |
|---|---|---|---|---|
| Hepes | 65 | 58,909 | 32 | 66 |
| Sodium Acetate | 95 | 50,951 | 24 | 30 |

Example 4

Optimization of Truncated Furin Purification on CAPTO MMC™ Columns by Modification of Conductivity CAPTO MMC™ columns were loaded with 70,000-100,000 U furin/mg gel. Loading solution was dialyzed against 10 mM sodium acetate, 1 mM $CaCl_2$, pH 6.0 resulting in a conductivity of approximately 1 mS/cm. Truncated furin losses in the flow-through and wash fractions of the CAPTO MMC™ column could be substantially reduced from approximately 17% to a not detectable level by adjusting the conductivity to 1 mS/cm. Moreover, column load could be increased up to nearly 100,000 U furin/mL gel (Table 4). A substantial truncated furin break-through was observed after application of 150,000 U furin/mL gel. However, it can be expected that the column load can be increased to 150,000 U/mL gel during optimization for large scale preparation.

Table 4. Purification of Truncated Furin on CAPTO MMC™ Columns at a Conductivity of 1 mS/cm

TABLE 4

Purification of Truncated Furin on CAPTO MMC ™ Columns
at a Conductivity of 1 mS/cm

| Furin Load (U/mL Gel) | Recovery (%) | Spec. Activity (U/mg) | Purification (Factor) | CHO-Protein Removal (Factor) |
|---|---|---|---|---|
| 105,700 | 19 | 57,692 | 23.7 | 18.8 |
| 70,400 | 97 | 96,896 | 37.7 | 29.4 |
| 74,700 | 94 | 138,299 | 55.3 | 41.8 |
| 91,500 | 90 | 140,866 | 53.8 | n.d. |
| Mean | 61 | 87,474 | 34.4 | 22.9 |

Example 5

Recovery of Truncated Furin from CAPTO MMC™ Columns by Gradient or Step Elution

Figure 1:
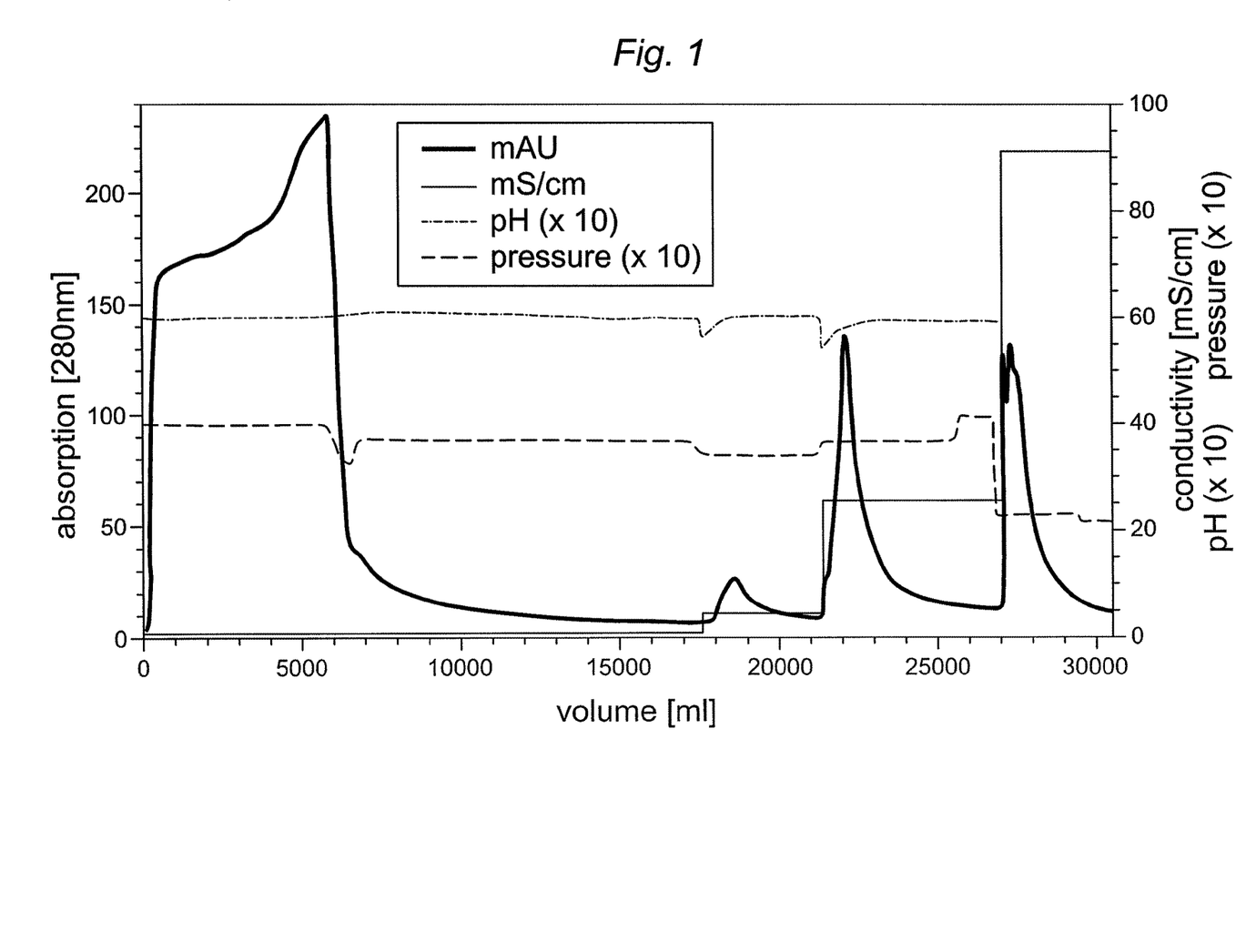
FIG. 1 shows purification of a truncated furin by CAPTO MMC™ column chromatography using step elution (Example 5)
Figure 2:
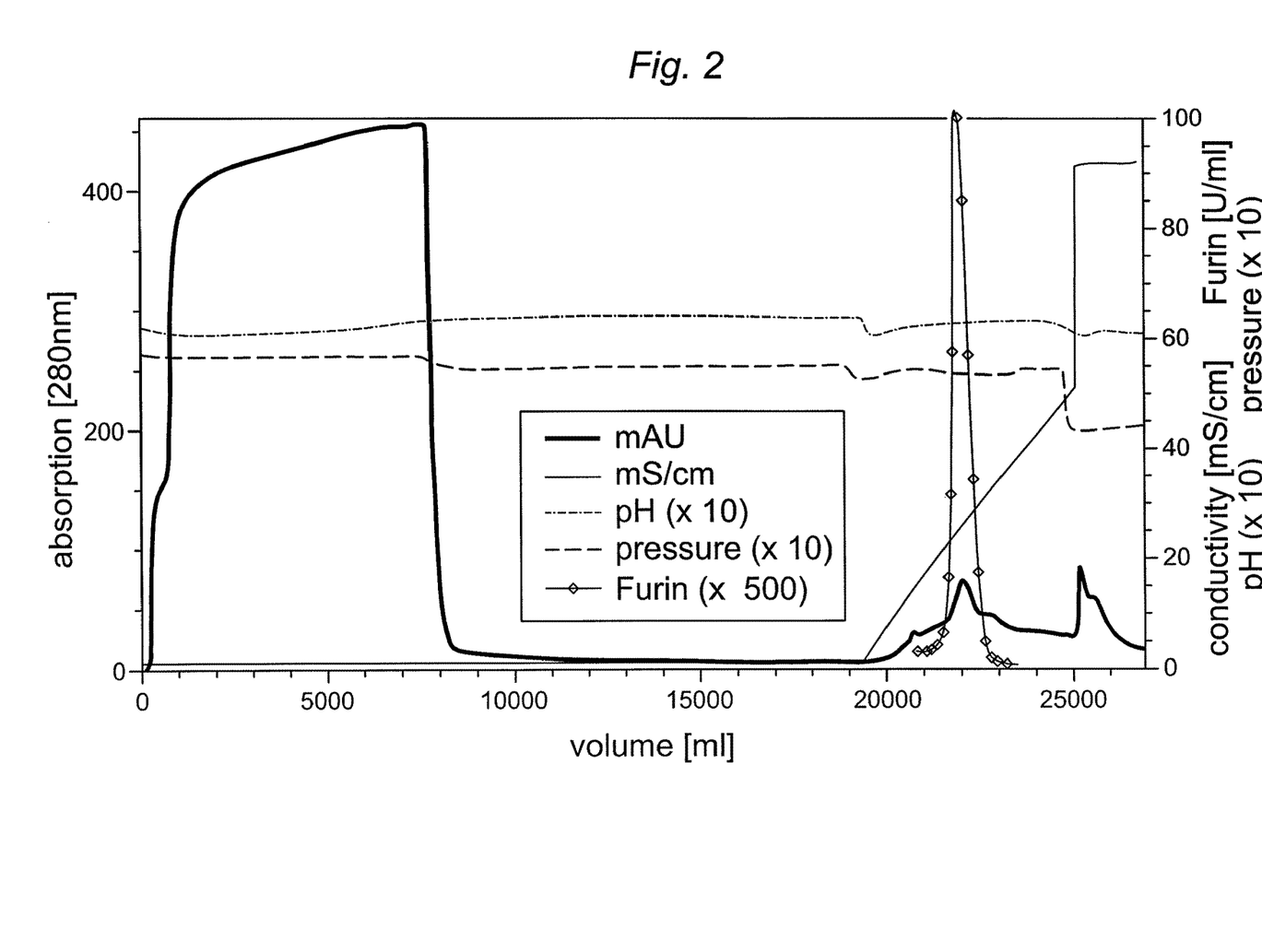
FIG. 2 shows purification of a truncated furin by CAPTO MMC™ column chromatography using gradient elution (Example 5)

To increase robustness of the column chromatography, the sodium chloride gradient for elution of truncated furin was replaced by step gradients. Approximately 80,000 U/mL gel (gradient) and 30,000 U/mL gel (step gradient) of truncated furin (dialyzed against 10 mM sodium acetate, 1 mM $CaCl_2$ pH 6.0) were loaded onto a CAPTO MMC™ column. The chromatography runs were carried out with 10 mM sodium acetate/1 mM $CaCl_2$ buffer at pH 6. In addition to the gradient elution of 0-500 mM NaCl in sodium acetate loading buffer within 15 column volumes an additional washing step at 30 mM sodium chloride containing equilibration buffer and elution with 230 mM sodium chloride in the same buffer was carried out. The column was washed with 30 volumes of equilibration buffer and then with 10 volumes of equilibration buffer containing 30 mM sodium chloride. Truncated furin was eluted with 14 volumes of equilibration buffer containing 230 mM sodium chloride. The first 3 volumes of the 230 mM sodium chloride eluate were collected. This resulted in a lower purification factor and lower absolute truncated furin concentration in the eluate. The mean of 2 experiments, respectively, is shown in Table 5. In contrast to this the peak collection of the eluted truncated furin (FIG. 1) from the step elution was better as compared to the peak collection obtained from gradient elution (FIG. 2).

Table 5. Gradient or Step Gradient Elution of Truncated Furin from CAPTO MMC™ Columns

TABLE 5

Gradient or Step Gradient Elution of Truncated
Furin from CAPTO MMC ™ Columns

| Elution | Recovery (%) | Spec. Activity (U/mg) | Purification (Factor) |
|---|---|---|---|
| Gradient | 92 | 139,592 | 55 |
| Step Gradient | 92 | 31,725 | 14 |

Example 6

Additional Arginine-Sepharose Column Purification of Truncated Furin Eluted from CAPTO MMC™ Columns A at least 20% pure truncated furin preparation obtained after CAPTO MMC™ chromatography had already an purification degree allowing on-column maturation of pro-VWF. For a higher purification factor an additional Arginine-Sepharose chromatography purification can be carried out.

Figure 3:
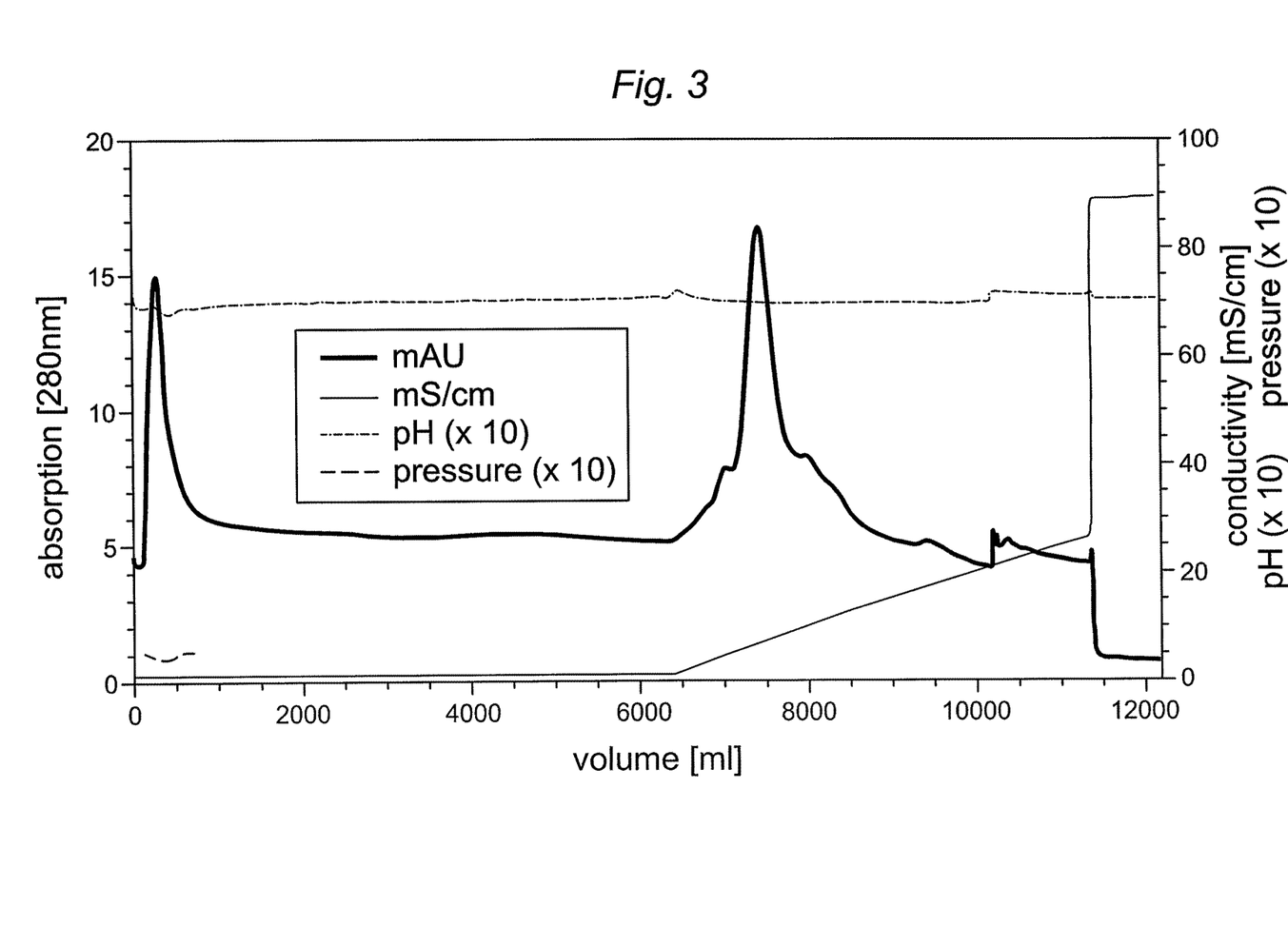
FIG. 3 shows purification of a truncated furin obtained from CAPTO MMC™ column chromatography with an additional Arginine Sepharose chromatography (Example 6)

A truncated furin containing eluate from the CAPTO MMC™ chromatography step was dialyzed against 50 mM Hepes buffer, 1 mM $CaCl_2$, pH 7.0 and approximately 33,000 U furin/mL gel were loaded onto an ARGININE SEPHAROSE™ 4B column (GE Healthcare) equilibrated in the same buffer. Truncated furin was eluted with a 0-250 mM NaCl gradient in equilibration buffer within 25 column volumes. The chromatography run is shown in FIG. 3. A truncated furin peak eluting at approximately 60 mM NaCl was concentrated 5-fold by ultrafiltration using a 10 kDa cutoff polysulfone membrane and adjusted to 150 mM NaCl. After sterile filtration on SARTOBRAN® P (Sartorius, Gottingen, Germany) truncated furin was stored at −20.degree. C. The specific activity of truncated furin was approximately 290,000+/−60,000 U/mg protein (n=3). The overall yield as compared to fermentation supernatant as starting material was approximately 50% (n=3), the total purification factor approximately 140, and the purity at least 90-95% as determined by COOMASSIE® staining before ultraconcentration (FIG. 4, lane 3) and after ultraconcentration (FIG. 4, lane 2).

According to the examples shown in the present invention the best method for purification of truncated furin is to adjust approximately 150 million units of a truncated furin concentrate (80,000-100,000 U/mL gel) to pH 6.0+/−0.1 and apply it to a 1.5 L BPG100/20 CAPTO MMC™ column equilibrated against 10 mM sodium acetate, 1 mM $CaCl_2$, pH 6.0. The column is washed with 30 volumes of equilibration buffer and then with 10 volumes of equilibration buffer containing 30 mM sodium chloride. Truncated furin is eluted with 14 volumes of equilibration buffer containing 230 mM sodium chloride. Collection of the first 3 volumes of the 230 mM sodium chloride eluate results in the most concentrated furin solution. If higher purification degrees are desired an additional Arginine Sepharose chromatography purification can be carried out.

---

What is claimed is:

1. A method of purifying a furin polypeptide or a furin polypeptide derivative having furin biological activity from a protein solution comprising the following steps:
   (a) binding the furin polypeptide or furin polypeptide derivative to a mixed cation exchange/hydrophobic interaction resin that binds the furin polypeptide or furin polypeptide derivative at pH 6.0, and
   (b) recovering the furin polypeptide or furin polypeptide derivative from the resin by elution.

2. The method of claim 1, characterized in that said furin polypeptide derivative is a truncated furin polypeptide.

3. The method of claim 2, characterized in that said truncated furin polypeptide is the furin polypeptide according to SEQ ID NO:1.

4. The method of claim 1, wherein the elution is step-wise elution.

5. The method of claim 1, wherein said furin polypeptide, or furin polypeptide derivative is bound to said mixed cation exchange/hydrophobic interaction resin in 10 mM sodium acetate, 1 mM $CaCl_2$ pH 6.0, washed with 30 mM sodium chloride, 10 mM sodium acetate, 1 mM $CaCl_2$ pH 6.0, and eluted with 230 mM sodium chloride, 10 mM sodium acetate, 1 mM $CaCl_2$ pH 6.0.

6. The method of claim 1, wherein said furin polypeptide, or furin polypeptide derivative is bound to said mixed cation exchange/hydrophobic interaction resin in 50 mM Hepes, 1 mM $CaCl_2$ pH 6.0, washed with 30 mM sodium chloride, 50 mM Hepes, 1 mM $CaCl_2$ pH 6.0, and eluted with 230 mM sodium chloride, 50 mM Hepes, 1 mM $CaCl_2$ pH 6.0.

7. The method of claim 1, wherein the elution is gradient elution.

8. The method of claim 7, wherein said gradient is 0-500 mM NaCl in 10 mM sodium acetate, 1 mM $CaCl_2$ pH 6.0.

9. A method of recovering a furin polypeptide or a furin polypeptide derivative having furin biologic activity comprising the following steps:
   (a) binding said furin polypeptide or furin polypeptide derivative to a mixed cation exchange/hydrophobic interaction resin,
   (b) eluting said furin polypeptide or furin polypeptide derivative from the mixed cation exchange/hydrophobic interaction resin,
   (c) binding the eluted furin polypeptide or furin polypeptide derivative to an Arginine-Sepharose resin, and
   (d) eluting said furin polypeptide or furin polypeptide derivative from the Arginine-Sepharose resin.

10. The method of claim 9, characterized in that said furin polypeptide derivative is a truncated furin polypeptide.

11. The method of claim 10, characterized in that said truncated furin polypeptide has the sequence shown in SEQ ID NO:1.

12. The method of claim 2, wherein said truncated furin polypeptide is bound to said mixed cation exchange/hydrophobic interaction resin in 10 mM sodium acetate, 1 mM $CaCl_2$ pH 6.0, washed with 30 mM sodium chloride, 10 mM sodium acetate, 1 mM $CaCl_2$ pH 6.0, and eluted with 230 mM sodium chloride, 10 mM sodium acetate, 1 mM $CaCl_2$ pH 6.0.

13. The method of claim 2, wherein said truncated furin polypeptide is bound to said mixed cation exchange/hydrophobic interaction resin in 50 mM Hepes, 1 mM $CaCl_2$ pH 6.0, washed with 30 mM sodium chloride, 50 mM Hepes, 1 mM $CaCl_2$ pH 6.0, and eluted with 230 mM sodium chloride, 50 mM Hepes, 1 mM $CaCl_2$ pH 6.0.

* * * * *

SEQUENCE LISTING

```
<160> NUMBER OF SEQ ID NOS: 3

<210> SEQ ID NO 1
<211> LENGTH: 577
<212> TYPE: PRT
<213> ORGANISM: Homo sapiens
<220> FEATURE:
<223> OTHER INFORMATION: subtilisin-like proprotein convertase (SPC)
      family member truncated human furin lacking C-terminal amino acids
      578-794 (paired basic amino acid cleavage enzyme (PACE)), secreted
      "shed furin"

<400> SEQUENCE: 1

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175
```

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
            195                 200                 205

Gly Val Cys Gly Val Gly Val Ala Tyr Asn Ala Arg Ile Gly Gly Val
            210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
            245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
            275                 280                 285

Phe Val Trp Ala Ser Gly Asn Gly Gly Arg Glu His Asp Ser Cys Asn
            290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
            325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
            355                 360                 365

Ala Ser Ala Pro Leu Ala Ala Gly Ile Ile Ala Leu Thr Leu Glu Ala
            370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
            405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
            435                 440                 445

Lys Cys Ile Ile Asp Ile Leu Thr Glu Pro Lys Asp Ile Gly Lys Arg
            450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
            485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
            515                 520                 525

Asn Asp Trp Ala Phe Met Thr Thr His Ser Trp Asp Glu Asp Pro Ser
            530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
            565                 570                 575

Gly

<210> SEQ ID NO 2
<211> LENGTH: 4

```
<212> TYPE: PRT
<213> ORGANISM: Artificial Sequence
<220> FEATURE:
<223> OTHER INFORMATION: furin-specific dibasic cleavage site
      fluorogenic substrate
<220> FEATURE:
<221> NAME/KEY: MOD_RES
<222> LOCATION: (1)...(1)
<223> OTHER INFORMATION: Arg modified by Boc
<220> FEATURE:
<221> NAME/KEY: MOD_RES
<222> LOCATION: (4)...(4)
<223> OTHER INFORMATION: Arg modified by 7-amino-4-methylcoumarin (AMC)

<400> SEQUENCE: 2

Arg Val Arg Arg
1

<210> SEQ ID NO 3
<211> LENGTH: 4
<212> TYPE: PRT
<213> ORGANISM: Artificial Sequence
<220> FEATURE:
<223> OTHER INFORMATION: Limulus Amebocyte Assay (LAL) endotoxin assay
      chromoogenic substrate S-2423
<220> FEATURE:
<221> NAME/KEY: MOD_RES
<222> LOCATION: (1)...(1)
<223> OTHER INFORMATION: Ile modified by acetyl group (Ac)
<220> FEATURE:
<221> NAME/KEY: MOD_RES
<222> LOCATION: (4)...(4)
<223> OTHER INFORMATION: Arg modified by para nitroaniline (pNA)

<400> SEQUENCE: 3

Ile Glu Gly Arg
1
```